(12) United States Patent
Bosch et al.

(10) Patent No.: US 9,546,254 B2
(45) Date of Patent: Jan. 17, 2017

(54) USE OF AN LLDPE COMPOSITION IN HEALTH CARE APPLICATIONS

(71) Applicant: SAUDI BASIC INDUSTRIES CORPORATION, Riyadh (SA)

(72) Inventors: Josephina Jacobina Antoinette Bosch, Sittard (NL); Gert Jan Elisa Coun, Dilsen-Stokkem (BE); Roelof Franciscus Gerardus Maria De Vos, Bunde (NL); Patrick Elisabeth Luc Voets, Geleen (NL)

(73) Assignee: SAUDI BASIC INDUSTRIES CORPORATION, Riyadh (SA)

( * ) Notice: Subject to any disclaimer, the term of this patent is extended or adjusted under 35 U.S.C. 154(b) by 0 days.

(21) Appl. No.: 14/436,025

(22) PCT Filed: Oct. 15, 2013

(86) PCT No.: PCT/EP2013/071484
§ 371 (c)(1),
(2) Date: Apr. 15, 2015

(87) PCT Pub. No.: WO2014/060390
PCT Pub. Date: Apr. 24, 2014

(65) Prior Publication Data
US 2015/0267013 A1   Sep. 24, 2015

(30) Foreign Application Priority Data
Oct. 16, 2012   (EP) .................................... 12007162

(51) Int. Cl.
| | |
|---|---|
| *C08K 3/18* | (2006.01) |
| *C08J 5/18* | (2006.01) |
| *C08K 3/22* | (2006.01) |
| *C08L 23/08* | (2006.01) |
| *A61L 31/02* | (2006.01) |
| *A61L 31/04* | (2006.01) |

(52) U.S. Cl.
CPC .............. *C08J 5/18* (2013.01); *A61L 31/028* (2013.01); *A61L 31/041* (2013.01); *A61L 31/048* (2013.01); *C08K 3/22* (2013.01); *C08L 23/0815* (2013.01); *C08J 2323/08* (2013.01); *C08J 2423/08* (2013.01); *C08K 2003/2296* (2013.01); *C08L 2203/02* (2013.01)

(58) Field of Classification Search
CPC ....... C08J 5/18; C08J 2323/08; C08J 2423/08; A61L 31/048; A61L 31/028; A61L 31/041

USPC ......................................................... 524/432
See application file for complete search history.

(56) References Cited

U.S. PATENT DOCUMENTS

| | | | | |
|---|---|---|---|---|
| 4,686,125 | A * | 8/1987 | Johnston | A61J 1/10 383/113 |
| 5,132,344 | A * | 7/1992 | Matteodo | C08K 3/22 524/101 |
| 2005/0087914 | A1* | 4/2005 | Rhee | C08J 5/18 264/564 |
| 2007/0100047 | A1* | 5/2007 | Sukhadia | C08L 23/08 524/394 |
| 2012/0202942 | A1* | 8/2012 | Mavridis | C08J 5/18 524/528 |

FOREIGN PATENT DOCUMENTS

| | | |
|---|---|---|
| EP | 2319686 A1 | 5/2011 |
| WO | 2005042625 A1 | 5/2005 |
| WO | 2007055977 A1 | 5/2007 |
| WO | 2012109246 A1 | 8/2012 |

OTHER PUBLICATIONS

Cooke et al. "Addition of Branched Molecules and High Molecular Weigh Molecules to Improve Optical Properties of LLDPE Film," Journal of Plastic Film & Sheeting, vol. 5 (Oct. 1989), pp. 290-307.
International Search Report for International Application No. PCT/EP2013/071484; International Filing Date: Oct. 15, 2013; Date of Mailing: Jan. 16, 2014; pp. 1-5.
Peacock, "Handbook of Polyethylene: Structures, Properties, and Applications," (2000) Marcel Dekker; pp. 43-66.
Written Opinion of the International Searching Authority for International Application No. PCT/EP2013/071484; International Filing Date: Oct. 15, 2013; Date of Mailing: Jan. 16, 2014; pp. 1-7.

* cited by examiner

*Primary Examiner* — Hui Chin
(74) *Attorney, Agent, or Firm* — Cantor Colburn LLP

(57) ABSTRACT

The invention relates to the use of a composition comprising linear low density polyethylene and an inorganic acid in health care applications. The inorganic acid may be selected from the group consisting of aluminum oxide, zinc oxide, calcium oxide, calcium hydroxide, magnesium oxide, magnesium hydroxide, hydrotalcites and any mixtures of any one of these inorganic acids. Furthermore, the composition may further comprise low density polyethylene, for example in a weight ratio of 10/90 to 50/50 with linear low density polyethylene.

17 Claims, No Drawings

USE OF AN LLDPE COMPOSITION IN HEALTH CARE APPLICATIONS

CROSS REFERENCE TO RELATED APPLICATIONS

This application is a 371 of International Application No. PCT/EP2013/071484, filed Oct. 15, 2013 which claims priority to European Application No. 12007162.6, filed Oct. 16, 2012 which are hereby incorporated by reference in their entirety.

The invention is directed to the use of a linear low density polyethylene (LLDPE) composition in health care applications.

The healthcare market is continuously searching for improved polymer grades for rigid and flexible products, ensuring a consistent approach to the medical and healthcare market. Because of the material properties polyethylene is used in many health care applications. As an example, a film must have the required mechanical properties such as tear resistance, impact resistance and tensile strength, the required chemical resistance such as environmental stress crack resistance, the required optical properties such as gloss, haze and clarity, the required sealing and hot tack properties. Furthermore the polymer to be applied in such healthcare applications must be compliant to the legal requirements such as the European Pharmacopoeia standard tests and USP Class VI compliant.

It is the object of the present invention to provide a polymer composition that meets the legal requirements and also the technical requirements of a wide variety of health care applications.

The present invention is directed to the use of a composition comprising linear low density polyethylene and an inorganic acid scavenger in health care applications.

In another embodiment, the invention is directed to the composition comprising linear low density polyethylene and an inorganic acid scavenger for use in health care applications.

Without wishing to be bound by theory, the inorganic acid scavenger neutralizes the catalyst residues from the catalyst used in the preparation of the LLDPE.

Examples of suitable inorganic acid scavengers include aluminium oxide, zinc oxide, calcium oxide, calcium hydroxide, magnesium oxide, magnesium hydroxide, hydrotalcites, as for example commercially available as DHT4A and mixtures of any one of these inorganic acid scavengers. Therefore, the invention also relates to the use of a composition comprising linear low density polyethylene and inorganic acid scavenger, wherein the inorganic acid scavenger is selected from the group of aluminium oxide, zinc oxide, calcium oxide, calcium hydroxide, magnesium oxide, magnesium hydroxide, hydrotalcites and any mixtures of any one of these inorganic acid scavengers. Preferably zinc oxide, calcium oxide, magnesium oxide or any mixtures of any of these oxides are used as inorganic acid scavenger. For example, the inorganic acid scavenger is selected from the group of zinc oxide, calcium oxide and magnesium oxide. Most preferably, the inorganic acid scavenger is zinc oxide.

The composition comprising linear low density polyethylene and an inorganic acid scavenger meets the requirements of the European Pharmacopoeia standard tests as described herein.

In order to meet the requirements of the European Pharmacopoeia, components may not leach out of the article and may not be extractable from the article in an amount above the limits set by the European Pharmacopoeia.

This polymer composition may suitably be used in health care applications because this composition may have one or more of the following advantages: good mechanical properties, mechanical properties, chemical resistance, and/or hot tack properties.

The LLDPE composition according to the invention can be applied in healthcare applications such as pharmacy pouches/bags because of the obtained puncture resistance and the hot tack properties, tubes because of the obtained Environmental Stress Crack Resistance (ESCR), multilayer medical films, intermediate packaging for example for sharp objects in the operating room and in building blocks for example LLDPE and LDPE blends for infusion bags and bottles.

Therefore, the invention also relates to the use of the invention, wherein the composition is in the form of a pharmacy pouch, tube, multilayer film, intermediate packaging, infusion bag or bottle, or a medical device, for example any medical device where the typical LLDPE properties can be of advantage.

Therefore, in another aspect, the invention also relates to pharmacy pouch, tube, multilayer film, intermediate packaging, infusion bag or a bottle prepared from a composition as described herein.

The use of the composition according to the invention results in stearate free compositions to be applied for example in dialysis applications. Furthermore, the composition of the invention provides compositions that preferably do not contain compounds from a living source, such as an animal source, for example a bovine source or a vegetable source.

The LLDPE composition according to the invention results in an excellent final product not only from a mechanical point of view but also from a sustainability one because down gauging is possible and therefore less material is used in the final package.

The pharmaceutical packaging market can be divided into primary packaging that is in direct contact with the active pharmacy ingredient and includes blister packs, fluid bags, pouches, bottles, vials and ampoules and into secondary packaging which includes every part of the total concept or medical device that is not in direct contact with the packed drug or fluid. The polymer composition according to the invention provides a low interaction between the packaging and the active pharmacy ingredient.

The linear low density polyethylene component of the composition is a low density polyethylene copolymer comprising ethylene and a $C_3$-$C_{10}$ alpha-olefin co monomer. Suitable alpha-olefin co monomers include butene, hexene, 4-methyl pentene and octene.

According to a preferred embodiment of the invention the co monomer is hexene and octene.

According to a preferred embodiment of the invention the co monomer is hexene.

Preferably, the alpha-olefin co monomer is present in an amount ranging between 5 and 20 percent by weight of the ethylene-alpha olefin copolymer. More preferably this amount ranges between 7 and 15 percent by weight. For example, the amount of alpha-olefin co monomer is at least 5, for example at least 7 and/or at most 20, for example at most 15 percent by weight.

Preferably the linear low density polyethylene has a density in the range between 915 kg/m³ and 930 kg/m³.

More preferably the linear low density polyethylene has a density in the range between 915 kg/m³ and 920 kg/m³

Preferably the linear low density polyethylene has a melt flow rate as determined using ISO1133 (2.16 kg/190° C.) in the range between 0.33 and 30 g/10 minutes.

Preferably the inorganic natural acid scavenger additive is added in an extruder after polymerisation of LLDPE.

The optimal amount of the inorganic acid scavenger depends on the catalyst system selected for the polymerisation of LLDPE and on the efficiency of that catalyst system during the production of LLDPE. Generally, the compositions of the invention may contain an amount of inorganic acid scavenger in the range from 100 to 1500 ppm, for example in the range from 400 to 800 ppm, for example in the range from 500 to 750 ppm, for example in the range from 600 to 700 ppm, for example in the range from 300 to 500 ppm, for example in the range from 315 to 385 ppm.

The composition may consist of LLDPE and an inorganic acid scavenger, for example in an amount of 100 to 1500 ppm on the total composition, but LLDPE may also be present in an amount of 50 to 99 wt %, for example in an amount of at most 95 wt %, for example at most 90 wt %, for example at most 85 wt %, for example at most 75 wt % based on the total composition.

The composition may further comprise low density polyethylene (LDPE), for example in a weight ratio of LDPE to LLDPE of 10/90 to 50/50, for example 20/80 to 50/50, for example 25/75 to 50/50. The presence of LDPE in the composition of the invention may have the advantage of increased processability and/or increased optical properties.

Preferably the density of the LDPE ranges between 915 kg/m$^3$ and 928 kg/m$^3$. Preferably the LDPE has a melt flow rate as determined using ISO1133 (2.16 kg/190° C.) in the range between between 0.2 and 3 g/10 min.

The polymer composition may also comprise additives, for example process stabilisers, antioxidants and light stabilizers, for example UV stabilizers.

Suitable examples of these additives include for example tris(2,4-di-t-butyl phenyl) phosphite, octadecyl 3,5-bis(1,1-dimethyl)-4-hydroxybenzene propionate and pentaerytritol tetrakis(3-(3,5-di-t-butyl-4-hydroxyphenol) propionate.

The polymer composition may also contain appropriate amounts of other additives such as for example fillers, antioxidants, pigments, antistatic agents and polymers depending on the specific use.

The production processes of LLDPE and LDPE are summarised in "Handbook of Polyethylene" by Andrew Peacock (2000; Dekker; ISBN 0824795466) at pages 43-66. The catalysts can be divided in three different subclasses including Ziegler Natta catalysts, Phillips catalysts and single site catalysts. The latter class is a family of different classes of compounds, metallocene catalysts being one of them. As elucidated at pages 53-54 of said Handbook a Ziegler-Natta catalysed polymer is obtained via the interaction of an organometallic compound or hydride of a Group I-III metal with a derivative of a Group IV-VIII transition metal. An example of a (modified) Ziegler-Natta catalyst is a catalyst based on titanium tetra chloride and the organometallic compound triethylaluminium. A difference between metallocene catalysts and Ziegler Natta catalysts is the distribution of active sites. Ziegler Natta catalysts are heterogeneous and have many active sites. Consequently polymers produced with these different catalysts will be different regarding for example the molecular weight distribution and the comonomer distribution.

The various processes may be divided into solution polymerisation processes employing homogeneous (soluble) catalysts and processes employing supported (heterogeneous) catalysts. The latter processes include both slurry and gas phase processes.

According to a preferred embodiment of the present invention the LLDPE has been obtained with gas phase polymerisation in the presence of a metallocene catalyst or a Ziegler Natta catalyst.

Although the invention has been described in detail for purposes of illustration, it is understood that such detail is solely for that purpose and variations can be made therein by those skilled in the art without departing from the spirit and scope of the invention as defined in the claims.

It is further noted that the invention relates to all possible combinations of features described herein, preferred in particular are those combinations of features that are present in the claims.

It is further noted that the term 'comprising' does not exclude the presence of other elements. However, it is also to be understood that a description on a product comprising certain components also discloses a product consisting of these components. Similarly, it is also to be understood that a description on a process comprising certain steps also discloses a process consisting of these steps.

The invention is now elucidated by way of the following examples, without however being limited thereto.

EXAMPLE 1

European Pharmacopeia Tests

SABIC® LLDPE PCG6118NE was used. This grade was prepared by melt-mixing an LLDPE powder having a density of 918 kg/m$^3$ and a melt flow rate (ISO1133, 2.16 kg/190° C.) of 0.9 g/10 minutes. with Zn stearate (ZnSt; final concentration in the LLDPE composition 500 ppm) and anti-oxidants (final concentration in the LLDPE composition 1000 ppm) in a twin screw extruder. The example was repeated, but instead of ZnSt, ZnO (final concentration in the LLDPE composition 350 ppm) was used.

Sample 1 as referred herein is the LLDPE grade with 350 ppm ZnO. Sample A as referred herein the LLDPE grade with 500 ppm Zn stearate (ZnSt).

The standard tests according to European Pharmacopeia 7.0, volume 1, January 2011; §3.1.3—Polyolefines were conducted on Sample 1 (SABIC® LLDPE PCG6118NE containing 350 ppm zinc oxide) and Sample A (SABIC® LLDPE PCG6118NE containing 500 ppm zinc stearate).

Identification was done by Fourier transform infrared spectroscopy (FTIR) by attenuated total reflection (ATR). The identification of the material was done as described in European Pharmacopeia 7.0, volume 1, January 2011; §3.1.3—Polyolefines.

IR Absorption:

Maxima at 2920 cm$^{-1}$, 1475 cm$^{-1}$, 1465 cm$^{-1}$, 1380 cm$^{-1}$, 1170 cm$^{-1}$, 735 cm$^{-1}$ and 720 cm$^1$. The spectra obtained were identical to a reference of linear low density polyethylene.

The results are presented in Table 1 below:

TABLE 1

Results of the standard test of the European Pharmacopeia on an LLDPE sample with zinc oxide (sample 1) and on a sample with zinc stearate (sample A).

| Analysis | Dimensions | Specification | Results sample 1 | Results sample A |
|---|---|---|---|---|
| Appearance: | | | | |
| clear | | | clear | clear |
| colorless | | | colorless | colorless |
| Acidity | ml; 0.01N NaOH | ≤1.5 | <0.05 | <0.05 |
| alkalinity | Ml; 0.01N HCl | ≤1.0 | <0.05 | <0.05 |
| absorbance | — | ≤0.2 | <0.05 | <0.05 |

TABLE 1-continued

Results of the standard test of the European Pharmacopeia on an LLDPE sample with zinc oxide (sample 1) and on a sample with zinc stearate (sample A).

| Analysis | Dimensions | Specification | Results sample 1 | Results sample A |
|---|---|---|---|---|
| Reducing substances | Ml; 0.01N thio | ≤3.0 | 0.20 | 0.30 |
| Sulphated ash | % (m/m) | ≤1.0 | 0.05 | <0.01 |
| Aluminium | Mg/kg | ≤1 | <0.05 | 0.13 |
| Heavy metals | Mg/kg | ≤2.5 | <2.5 | <2.5 |
| Titanium | mg/kg | ≤1 | <0.05 | <0.05 |
| Zinc | mg/kg | ≤1 | <0.05 | 1.1 |
| Soluble in hexane | % (m/m) | ≤5 | 0.9 | 1.2 |

As can be seen from the above table, Sample 1 comprising a linear low density polyethylene and an inorganic acid scavenger for example zinc oxide passes all standard tests of the European Pharmacopeia, whereas sample A comprising a linear low density polyethylene and an organic acid does not pass the test for zinc as the limit according to the specification is 1 and the value tested is 1.1.

EXAMPLE 2

Mechanical Properties and Hot Tack

Of sample 1 (SABIC® LLDPE PCG6118NE containing 350 ppm zinc oxide) and of sample 2 (SABIC® LDPE PCG01 having a melt flow rate of 0.75 g/10 minutes and a density of 925 kg/m³, films were prepared of different thickness (50 and 100 μm) at a blow up ratio of 3 (BUR) using a Kühne blow film line equipped with 35 mm diameter extruder with a 120 mm die and a die gap of 1.5 mm. The machine was operated at 25 kg/h. Barrel temperature profiles were ramped from 40° C. at the feed section to 200° C. at the die.

The properties of the films are presented in table 2.

As can be seen from Table 2, the mechanical properties of the LLDPE film containing an inorganic acid scavenger are good and in some cases even better than the properties of the LDPE film.

Furthermore, the hot tack strength of the films was also measured (according to ASTM F1921). The results of these measurements are presented in table 3.

TABLE 2

Film properties of sample 1 (SABIC® LLDPE PCG6118NE containing 350 ppm zinc oxide) and of sample 2 (SABIC® LDPE PCG01) without additives.

|  |  |  | #1 | #2 | #3 | #4 |
|---|---|---|---|---|---|---|
|  |  |  | Sample 2 | Sample 2 | Sample 1 | Sample 1 |
| film thickness |  | μm | 100 | 50 | 100 | 50 |
| Elmendorf (N/mm [kJ/m2]) ASTM D1922/ ISO 6383-2 |  |  |  |  |  |  |
| tear strength | TD | N/mm | 47.2 | 32.6 | 255.2 | 161.5 |
| tear strength | MD | N/mm | 26.7 | 30.7 | 219.1 | 212.4 |
| Tensile test ASTM D822 [500 mm/min] |  |  |  |  |  |  |
| thickness | TD | Mm | 107.5 | 51.67 | 101 | 50.33 |
| thickness | MD | Mm | 107.33 | 52.5 | 106.17 | 48.5 |
| stress at yield | TD | N/mm² | 12 | 11.8 | 12.5 | 12.1 |
| stress at yield | MD | N/mm² |  | 11.9 | 11.7 |  |
| elongation at yield | TD | % | 15.3 | 13.3 | 15.2 | 13.4 |
| elongation at yield | MD | % |  |  | 19.6 | 22 |
| stress at break | TD | N/mm² | 19.5 | 22.4 | 49 | 48.3 |
| stress at break | MD | N/mm² | 22.1 | 20.5 | 44.6 | 52.2 |
| elongation at break | TD | % | 555 | 574 | 900 | 832 |
| elongation at break | MD | % | 557 | 307 | 908 | 731 |
| Modulus ASTM 882 |  |  |  |  |  |  |
| modulus of elasticity | TD | N/mm² | 175.5 | 179 | 206.1 | 205.4 |
| modulus of elasticity | MD | N/mm² | 177.3 | 180.4 | 180.7 | 186.7 |
| Impact strength ASTM D1709 A Monsanto Dart |  | g/μm | 2.5 | 3.5 | 8.1 | 7.5 |
| Puncture resistance ASTM D 5748-95 |  |  |  |  |  |  |
| energy/thickness Impact resistance | | J/m | 604 | 727 | 676 | 981 |
| VEM ISO7765-2 |  | kJ/m | 6.1 | 6 | 11.7 | 10.9 |

TABLE 3

| Hot tack strength | | | | |
|---|---|---|---|---|
| Hot tack strength ASTM F1921 (N/15 mm) | Sample 2 100 μm | Sample 2 50 μm | Sample 1 100 μm | Sample 1 50 μm |
| 60° C. | 0.1 | 0.1 | 0.2 | 0.1 |
| 65° C. | 0.1 | 0.1 | 0.2 | 0.1 |
| 70° C. | 0.1 | 0.1 | 0.2 | 0.1 |
| 75° C. | 0.1 | 0.1 | 0.2 | 0.1 |
| 80° C. | 0.1 | 0.1 | 0.1 | 0.2 |
| 85° C. | 0.1 | 0.1 | 0.1 | 0.2 |
| 90° C. | 0.1 | 0.1 | 0.1 | 0.2 |
| 95° C. | 0.1 | 0.2 | 0.2 | 0.4 |
| 100° C. | 0.3 | 0.2 | 0.2 | 0.6 |
| 105° C. | 0.6 | 0.5 | 0.6 | 0.9 |
| 110° C. | 0.7 | 0.5 | 1.9 | 1.5 |
| 115° C. | 0.7 | 0.2 | 2.3 | 1.5 |
| 120° C. | 0.67 | 0.1 | 2 | 2 |
| 125° C. | 0.6 | 0.1 | 1.6 | 1.4 |
| 130° C. | 0.5 | 0.1 | 0.3 | 0.6 |
| 135° C. | 0.1 | 0.1 | — | 0.9 |
| 140° C. | 0.1 | 0.1 | — | 1.6 |

As can be seen from table 3, the composition comprising LLDPE and an inorganic acid scavenger showed an increase in hot tack strength as compared to LDPE, which makes the LLDPE composition beneficial for use in many health care applications.

EXAMPLE 3

Blends of LLDPE and LDPE

Granulate of SABIC® LLDPE PCG6118NE containing 350 ppm zinc oxide was mixed with granulate of SABIC® LDPE2100TN00 containing no additives in a 70/30 or 30/70 weight ratio and fed to the extruder of the Kühne blown film line. The extruder had a 35 mm barrier screw with a shearing and a mixing part, L=24D. The blown film line had a die of 120 mm, a die gap of 2.7 mm Films of 50 µm were prepared at a blow up ratio of 2.

The properties of the blends were measured as presented in Table 1 herein and compared to a film of 50 µm with 100% SABIC® LLDPE PCG6118NE containing 350 ppm zinc oxide and are presented in Table 4 below.

TABLE 4

Film properties of LLDPE containing ZnO and LDPE

| Description | Direction | Unit | Sample 1 | Sample 3 | Sample 4 |
|---|---|---|---|---|---|
| LLDPE PCG6118NE | | wt % | 100 | 70 | 30 |
| LDPE 2100TN00 | | wt % | 0 | 30 | 70 |
| Impact strength VEM | | kJ/m | 8.4 | 5.9 | 7.9 (3.9#) |
| $F_{max}$ | | N | 37 | 40 | 41 |
| Elmendorf tear strength | TD | N/mm | 270 | 184 | 54 |
| Elmendorf tear strength | MD | N/mm | 134 | 16 | 63 |
| Tensile test | | | | | |
| stress at yield | TD | N/mm$^2$ | 13.0 | 13.1 | 11.8 |
| stress at yield | MD | N/mm$^2$ | 11.9 | 13.0 | 16.3 |
| stress at break | TD | N/mm$^2$ | 53.0 | 44.6 | 30.0 |
| stress at break | MD | N/mm$^2$ | 56.4 | 42.7 | 40.4 |
| elongation at break | TD | % | 831 | 859 | 872 |
| elongation at break | MD | % | 659 | 603 | 206 (74#) |
| E-modulus of elasticity | TD | N/mm$^2$ | 247 | 269 | 259 |
| E-modulus of elasticity | MD | N/mm$^2$ | 207 | 236 | 270 |
| Puncture resistance | | | | | |
| energy at rupture | | mJ/mm | 659 | 648 | 707 |

\# = standard deviation
TD = translational direction
MD = machine direction

As can be seen from Table 4, blends of LLDPE and LDPE also have good mechanical properties. Furthermore, since this blend comprises an LDPE, which also meets the requirements of the European also the blends comply with the requirements of the European Pharmacopeia. Therefore, compositions comprising LLDPE, LDPE and an inorganic acid scavenger, for example zinc oxide are suitable for use in health care applications.

CONCLUSION

The results as presented herein show that a composition comprising a linear low density polyethylene and an inorganic acid scavenger is suitable for use in health care applications since it has good mechanical properties and passes the European Pharmacopeia tests.

Oxygen induction temperature (OIT) was measured according to D3895-95 at 200 degrees C. on granulate of SABIC® LLDPE PCG6118NE containing 6 ppm of ZnO and compared to the OIT of granulate of SABIC® LLDPE PCG6118NE containing 690 ppm of ZnO.

It was found that the OIT of SABIC® LLDPE PCG6118NE containing 6 ppm of ZnO was 9 min and that the OIT of SABIC® LLDPE PCG6118NE containing 690 ppm of ZnO was 60 min.

OIT is an indicator for how quickly a (LLD)PE degrades. The higher the OIT, the slower the degradation.

It has therefore been shown that the compositions of the invention show less degradation, i.e. are more stable than compositions not according to the invention. This is of particular importance in healthcare, where articles need to be able to withstand sterilization temperatures for a certain time and should not degrade during sterilization.

The invention claimed is:

1. A pharmacy pouch, infusion bag, an infusion bottle, or a medical device prepared from a composition comprising linear low density polyethylene and an inorganic acid scavenger, wherein the inorganic acid scavenger comprises zinc oxide, wherein the zinc oxide is present in an amount from an amount of 100 to 1500 ppm based on the total composition;
   wherein the composition is free of compounds from an animal source and free of compounds from a vegetable source;
   wherein the linear low density polyethylene comprises ethylene and a $C_3$-$C_{10}$ alpha-olefin comonomer; and
   wherein the linear low density polyethylene has a density in the range between 915 kg/m$^3$ and 930 kg/m$^3$.

2. The article of claim 1, wherein the alpha olefin comonomer is at least one of butene, hexene, 4-methyl pentene and octene.

3. The article of claim 1, wherein the alpha olefin comonomer is present in an amount between 5 and 20 percent by weight of the linear low density polyethylene.

4. The article of claim 1, wherein the amount of inorganic acid scavenger is 400 to 800 ppm.

5. The article of claim 1, wherein the amount of inorganic acid scavenger is 300 to 500 ppm.

6. The article of claim 1, wherein the linear low density polyethylene has a melt flow rate as determined using ISO1133 (2.16 kg/190° C.) in the range between 0.33 and 30 g/10 minutes.

7. The article of claim 1, wherein the composition is free of stearates, free of compounds from an animal source, and free of compounds from a vegetable source.

8. A healthcare article, comprising:
   a composition comprising linear low density polyethylene and zinc oxide, wherein the zinc oxide is present in an amount from an amount of 100 to 1500 ppm based on the total composition.

9. The article of claim 8, wherein the composition is free of stearates.

10. The article of claim 8, wherein the composition is free of compounds from an animal source and free of compounds from a vegetable source.

11. The article of claim 8, wherein the linear low density polyethylene comprises ethylene and a $C_3$-$C_{10}$ alpha-olefin comonomer.

12. The article of claim 11, wherein the alpha olefin comonomer is at least one of butene, hexene, 4-methyl pentene and octene.

13. The article of claim 11, wherein the alpha olefin comonomer is present in an amount between 5 and 20 percent by weight of the linear low density polyethylene.

14. The article of claim 8, wherein the linear low density polyethylene has a density in the range between 915 kg/m$^3$ and 930 kg/m$^3$.

15. The article of claim 8, wherein the amount of inorganic acid scavenger is 400 to 800 ppm.

16. The article of claim 15, wherein the amount of inorganic acid scavenger is 300 to 500 ppm.

17. The article of claim 8, wherein the linear low density polyethylene has a melt flow rate as determined using ISO1133 (2.16 kg/190° C.) in the range between 0.33 and 30 g/10 minutes.

* * * * *